United States Patent
Verwoerd et al.

(10) Patent No.: US 7,133,543 B2
(45) Date of Patent: Nov. 7, 2006

(54) AUTOMATED SCANNING METHOD FOR PATHOLOGY SAMPLES

(75) Inventors: Nico Peter Verwoerd, Hazerswoude-Rijndijk (NL); Johannes Vrolijk, Rijnsburg (NL); Wilhelmina E. Mesker, Noordwijk (NL); Willem C. R. Sloos, Hazerswoude-dorp (NL); Jan Bonnet, Leiden (NL); Padraig S. O'Kelly, Wylam (GB); Mark Gregson, Hexham (GB); Kevin Shields, Tyne & Wear (GB); Hendrikus J. Tanke, Rijnsburg (NL)

(73) Assignee: Applied Imaging Corporation, Santa Clara, CA (US)

( * ) Notice: Subject to any disclaimer, the term of this patent is extended or adjusted under 35 U.S.C. 154(b) by 878 days.

(21) Appl. No.: 10/165,770

(22) Filed: Jun. 6, 2002

(65) Prior Publication Data

US 2003/0012420 A1    Jan. 16, 2003

Related U.S. Application Data

(60) Provisional application No. 60/376,775, filed on Apr. 29, 2002, provisional application No. 60/298,227, filed on Jun. 12, 2001.

(51) Int. Cl.
  *G06K 9/00* (2006.01)
(52) U.S. Cl. ............... 382/128; 382/151; 382/293; 382/294
(58) Field of Classification Search ............ 382/128, 382/133–134, 151, 293, 294
  See application file for complete search history.

(56) References Cited

U.S. PATENT DOCUMENTS

| | | | |
|---|---|---|---|
| 3,533,744 A | 10/1970 | Unger | |
| 3,851,972 A | 12/1974 | Smith et al. | |
| 4,232,970 A | 11/1980 | Sawamura et al. | |
| 4,761,075 A | 8/1988 | Matsushita et al. | |
| 4,807,984 A | 2/1989 | Kurimura et al. | |
| 4,847,910 A | 7/1989 | Sakuraba et al. | |
| 5,428,690 A | 6/1995 | Bacus et al. | |
| 5,432,054 A | 7/1995 | Saunders et al. | |
| 5,473,706 A | 12/1995 | Bacus et al. | |
| 5,581,487 A | 12/1996 | Kelly et al. | |
| 5,793,969 A | 8/1998 | Kamentsky et al. | |
| 6,001,357 A | 12/1999 | Wong et al. | |
| 6,046,219 A | 4/2000 | Hanauske-Abel et al. | |
| 6,169,816 B1 | 1/2001 | Ravkin | |
| 6,259,807 B1 | 7/2001 | Ravkin | |
| 6,272,235 B1 | 8/2001 | Bacus et al. | |
| 6,292,596 B1 * | 9/2001 | Snyder et al. | 382/319 |
| 6,522,774 B1 * | 2/2003 | Bacus et al. | 382/133 |
| 6,524,798 B1 | 2/2003 | Goldbard et al. | |

* cited by examiner

*Primary Examiner*—Jingge Wu
*Assistant Examiner*—Tom Y. Lu
(74) *Attorney, Agent, or Firm*—Townsend and Townsend and Crew LLP

(57) ABSTRACT

Scanning and analysis of cytology and histology samples uses a flatbed scanner to capture images of the structures of interest such as tumor cells in a manner that results in sufficient image resolution to allow for the analysis of such common pathology staining techniques as ICC (immunocytochemistry), IHC (immunohistochemistry) or in situ hybridization. Very large volumes of such material are scanned in order to identify cells or clusters of cells which are positive or warrant more detailed examination, and if analysis at higher resolution is necessary, information regarding these positive events is transferred to a secondary microscope, such as a conventional scanning microscope, to allow further analysis and review of the selected regions of the slide containing the sample.

38 Claims, 5 Drawing Sheets

AUTOMATED SCANNING METHOD FOR PATHOLOGY SAMPLES

CROSS-REFERENCES TO RELATED APPLICATIONS

This application claims priority from the following two provisional applications, the entire disclosures of which, including any attached documents, are incorporated by reference in their entirety for all purposes:

Provisional Application No. 60/376,775, filed Apr. 29, 2002 of Padraig S. O'Kelly et al. titled "Automated Scanning Method for Pathology Samples;" and Provisional Application No. 60/298,227 filed Jun. 12, 2001 of Padraig S. O'Kelly et al. titled "Automated Scanning Method for Pathology Samples."

BACKGROUND OF THE INVENTION

This invention relates generally to the automated analysis of samples (specimens) such as biological samples having microscopic features, and more specifically to the use of a flatbed scanner in such analysis.

The desirability of analyzing lymph nodes of cancer patients for micrometastatic (tumor) cells is well established, both as a indicator of patient prognosis and as a possible guide as to the advisability of treatment with adjuvant therapy (chemotherapy/hormones). Unfortunately, current practice makes it impractical to examine an entire lymph node.

Typically, a lymph node is on the order of 5 mm in length. In routine pathology this node is cut in two and embedded in paraffin. This results in two (half) nodes embedded next to each other with a depth on the order of 2.5 mm. The current practice is to take sections of this material, stained with hematoxylin and eosin (H&E) which are then examined manually by a pathologist using a conventional microscope.

Routine diagnosis on sentinel nodes is performed by cutting six 4-µm sections at one level, but a number of recent papers have highlighted the inadequacy of such an approach. It has also been suggested to use immunohistochemical (IHC) staining and examining very substantial proportions of the entire node, and increases of between 7% and 35% in positive cases were reported. Thus, the implication is that current practice is missing this number of truly positive cases. Given that the lymph node status is a key element in decisions of post-operative therapy, this is clearly cause for concern.

However, even cutting at a distance of 8 µm and examining only every other section results in more than 150 sections to be analyzed. Assuming that three sections are placed on each slide, the node requires more than 50 slides. This is clearly out of the realm of manual inspection of the samples.

Automated microscopy is well established as a significant enhancement. A conventional microscope-based scanner (CMS) uses a computer controlled stage for scanning a sample and a digital recording camera to record an image of one or several relevant microscopic fields for subsequent analysis by the computer. For example, image analysis is used to distinguish tumor cells from disturbing artifacts such as dirt, debris, or other events that resemble the cells of interest. For this process, sufficient spatial resolution is required. That is, each object needs to be described with sufficient image elements (pixels) in order to facilitate proper recognition. Whereas the effectiveness of such systems in producing reproducible results has been successfully demonstrated in a number of applications, their performance is relatively slow (typically 20 minutes to scan 1 square cm).

With a lymph node section being on the order of 5–6 mm on a side, it would take on the order of 15–20 hours to scan the 150 lymph node sections prepared as described above. Thus, even current automated scanning systems do not have the throughput to make analysis of all, or even substantial parts, of the node practical. This is disturbing since current research indicates that such information derived from a substantial part of the node would provide a potentially significant increase in clinical sensitivity.

SUMMARY OF THE INVENTION

The present invention provides techniques for high-throughput automated analysis of samples such as biological samples having microscopic features.

In short, this is made possible by the use of a flatbed scanner in combination with automated image analysis. In a method of analyzing histology or cytology samples positioned on slides according to an embodiment, a plurality of slides are scanned with a flatbed scanner using a first set of scanner parameters (characterized by a first resolution) to capture first image data, which is used to determine the locations on the slides that potentially contain the samples. At least those portions of the slides that potentially contain the samples are scanned with the flatbed scanner using a second set of scanner parameters (typically at a second resolution that is higher than the first resolution) to capture second image data. The second image data is analyzed to produce what is referred to as candidate information, which includes coordinate information about candidate structures of interest in the sample.

The analysis may include testing whether two features in the second image data satisfy a proximity constraint. In one example, where the structures of interest are tumor cells whose cytoplasm expresses cytokeratin, the sample is treated in a manner that selectively stains cytoplasm expressing cytokeratin with a brown color (which corresponds to a certain region in color space), and is counterstained with hematoxylin, which stains cell nuclei with a blue color (that corresponds to different region in color space). Thus, a portion of the image containing a tumor cell could be expected to include one or more "brown" pixels within a predetermined distance of one or more "blue" pixels.

This candidate information is stored for later presentation, which may include transferring the coordinate information for candidate structures of interest to a secondary (typically higher magnification) system for further analysis of slides containing the candidate structures of interest. The secondary system may be a computer-controlled microscope, a non-scanning microscope, or even a scanner (typically having a higher resolution than the second resolution).

A further understanding of the nature and advantages of the present invention may be realized by reference to the remaining portions of the specification and the drawings.

DESCRIPTION OF SPECIFIC EMBODIMENTS

Overview

The present invention provides techniques for the scanning and analysis of large numbers of cytology and histology samples, using a flatbed scanner to capture images of the structures of interest (e.g., cells, groups of cells, and the like). The scanner provides sufficient image resolution to allow for the analysis of samples provided with one or more relevant markers to produce enough brightfield contrast to recognize structures of interest, including samples subjected to such common pathology staining techniques as ICC (immunocytochemistry), IHC (immunohistochemistry), or in situ hybridization.

A particular application is the detection of micrometastatic (tumor) cells in lymph nodes, but the invention can be used for many applications, especially when large numbers of samples need to be processed. Micrometastatic cells are often referred to as micrometastases or micromets.

Figure 1:
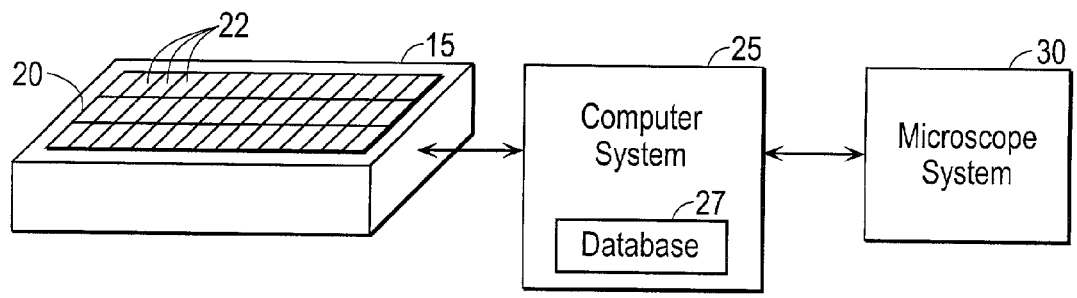
FIG. 1 is a schematic view of a system implementing an embodiment of the present invention.

FIG. 1 is a schematic view of a system 10 implementing an embodiment of the present invention. In short, the system includes a flatbed scanner 15 used to scan an array (or batch) 20 of sample slides 22, and a computer system 25 (with an associated database 27) to control the scanner and process the scanned digital image data for possible use in connection with further examination of the slides on a microscope 30. Microscope 30 is shown as being connected to computer 25, but as will be discussed below, this is not necessary. Microscope 30 is also referred to as a secondary system, and is typically capable of providing higher resolution than the highest resolution of scanner 15.

Figure 2:
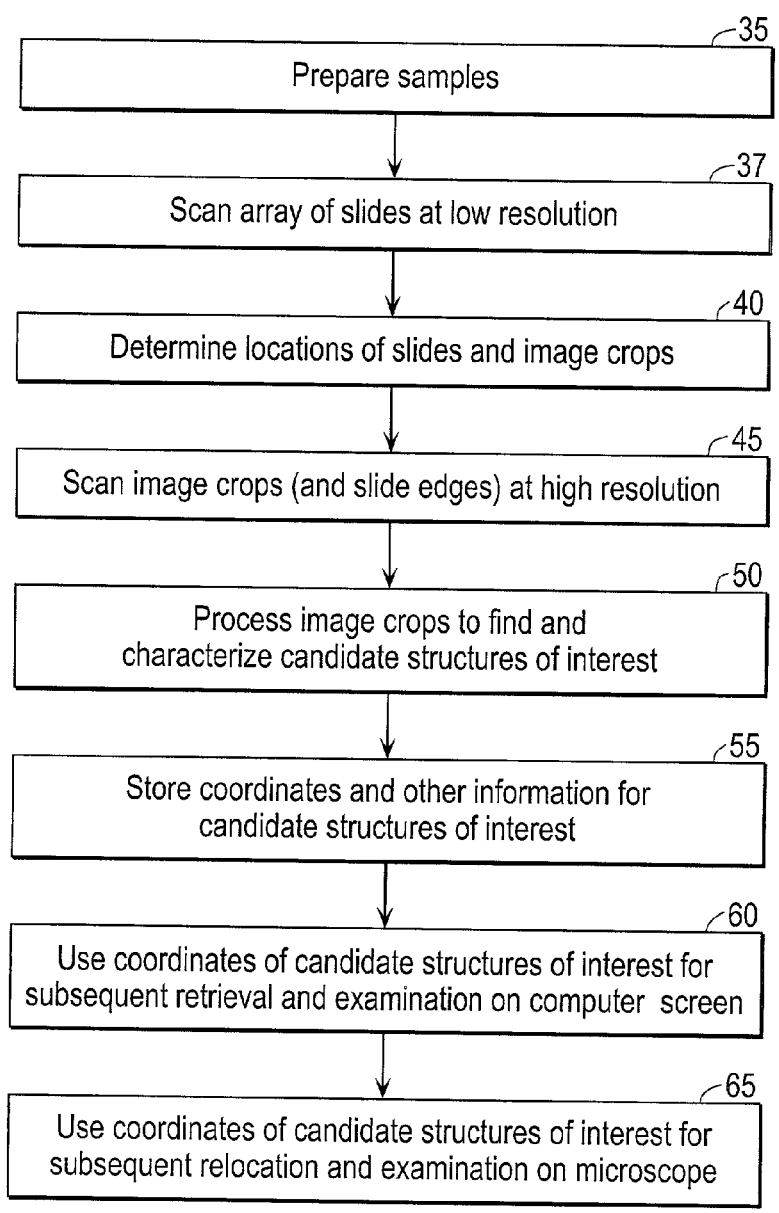
FIG. 2 is a high-level flowchart of a workflow in accordance with embodiments of the present invention.

FIG. 2 is a high-level flowchart of showing representative workflow in accordance with embodiments of the present invention. The workflow begins with sample preparation (step 35) where a number of samples are fixed to slides. An array of such slides are subjected to a low-resolution scan (step 37), and the scanned image is processed (step 40) to determine the locations of the slides on the scanner bed and the locations of image crops (i.e., portions of the overall scan area that will be subject to further scanning and analysis-typically about 50–75% of the slide area). This is followed by a high-resolution scan (step 45) of the image crops, and preferably also of additional regions in the vicinity of the horizontal and vertical slide edges.

Typical resolutions (in both directions) for the low-resolution scan and the high-resolution scans are on the order of 100–200 dots per inch (dpi) and 5000 dpi, respectively. The latter provides a sampling distance of about 5 μm, which corresponds to a magnification of about 2.5×. While this high resolution is at the high end of currently available flatbed scanners, microscopy is typically carried out at significantly higher resolutions.

This determination of the location of the slides and the image crops can be done automatically by image processing techniques to be discussed below, but can also be done interactively by an operator. For example, in an entirely manual approach, the operator would view the low-resolution scanned image on the computer system's display, and select the image crops by drawing rectangles around them using the computer system's pointing device. The operator could also designate the corners of the slides by clicking on them with the pointing device. This approach, while still consistent with the invention, is not preferred. A better approach would be to have the computer system perform the image processing to determine the location of the slides and image crops, and display dots on the slide corners and rectangles around the image crops. The operator could then verify that the computer system's findings were correct, select any image crops that were missed, and allow further processing to proceed. While this latter approach could be used on each batch of slides after it was scanned at low resolution, it is more likely to be used periodically as a spot check to determine whether any process parameters (e.g., the scanner settings) need to be adjusted.

The image crops are then subjected to image processing in order to find and characterize candidate structures of interest (step 50). A candidate structure of interest is often referred to simply as a "candidate." The characterization of a candidate typically includes the location (relative to the slide) as well as parameters denoting shape, size, and color of the candidate. The locations and characteristics of these candidates, along with the portion (fragment) of the image containing the candidate, are stored in the database (step 55). The collection of images is sometimes referred to as a gallery.

At this point, the workflow has encountered a break point, since the compiled information has been acquired substantially automatically, and subsequent steps may require skilled human intervention. In one scenario, the images stored in database 27 are retrieved and viewed by skilled personnel who are in a position to make initial value judgments and possibly provide annotations (step 60). For example, the person screening the images could flag some of the candidates in the images as needing further review on microscope 30, which can provide higher magnification than the effective magnification of the high-resolution scan. In another scenario, all candidates are slated for microscopic examination, and step 60 is skipped. Some or all slides containing candidates are then examined on the microscope (step 65). The coordinates stored in the database are used to facilitate relocation on the microscope. What is referred to as examination on the microscope could, in some implementations, be automatic acquisition on the scanning microscope of increased-resolution images of the candidates.

Scanner and Slide Holder

Scanner 15 is preferably a flatbed scanner, such as a model AgfaScan XY-15 Plus available from Agfa Corporation. This model has a tri-linear 8000-element CCD, and is capable of acquiring images at different resolutions up to a maximum optical resolution of 5000×5000 dpi, and is further capable of selectively acquiring portions of its overall scan field. This supports the functionality described above with respect to scanning all the slides at low resolution to determine the locations of the image crops, and then scanning the image crops at high resolution. This makes it possible to acquire the necessary information in less time and using less storage than scanning the entire scanner field at high resolution. While the particular scanner is capable of acquiring images in reflection or transmission mode, the particular example (examining lymph node sections with particular stains) acquires images in transmission mode. On the other hand, the reflection mode may be preferred to produce high-quality images of biological samples stained by reflective stains or even fluorescent dyes, both in combination with optical filters.

The sampling density was increased further to 5600 dpi by means of interpolation to improve image quality. The maximum scan area is 350×455 mm corresponding to A3+ format. However, the highest optical resolution is only achieved within the middle part of 232×455 mm. The maximum density range of the scanner is 0–3.9, resulting in a color depth of 16 bits per RGB color. Digitization was performed using the ColorExact software package from Agfa, which directs the scan mode, scan resolution, color calibration and dynamic range.

Figure 3A:
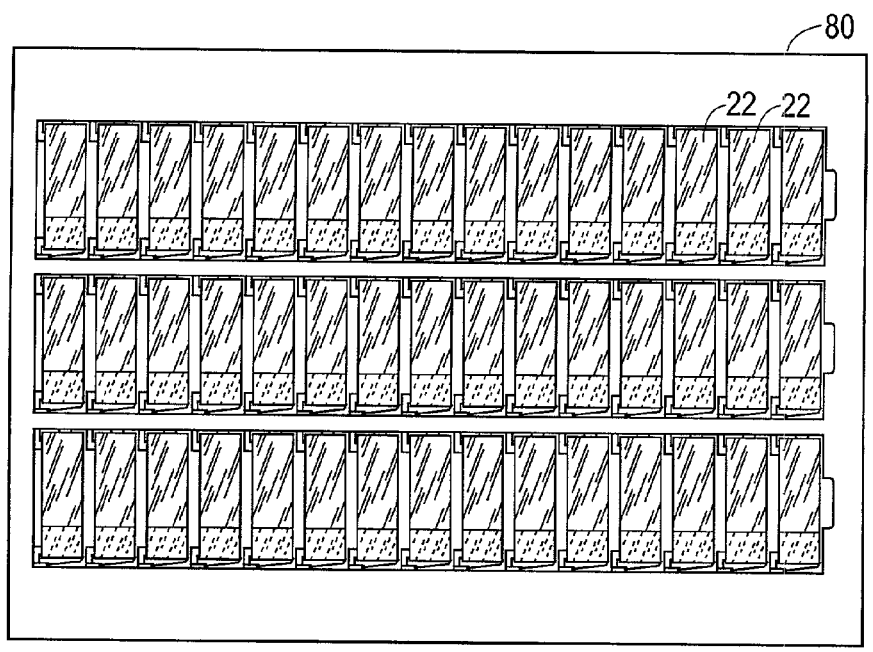
FIG. 3A is a plan view of a slide rack suitable for use in embodiments of the present invention.

FIG. 3A is a plan view of a slide rack 80 suitable used in a particular implementation. This particular slide rack is preferably molded in plastic such as polycarbonate, and is formed with 45 slide-receiving regions (denoted 82 in FIG. 3B). Typical slides are 1×3 inches (25.4×76.2 mm), and the total area occupied by the slide-receiving regions is on the order of 26×47 cm, which corresponds to having the samples on the slides located over the scanner's region of maximum resolution. This configuration is tailored to the particular scanner's A3+ scan bed and region of maximum resolution. Clearly, other slide holder configurations would be appropriate for other sizes of slides and scanner beds.

Figure 3B:
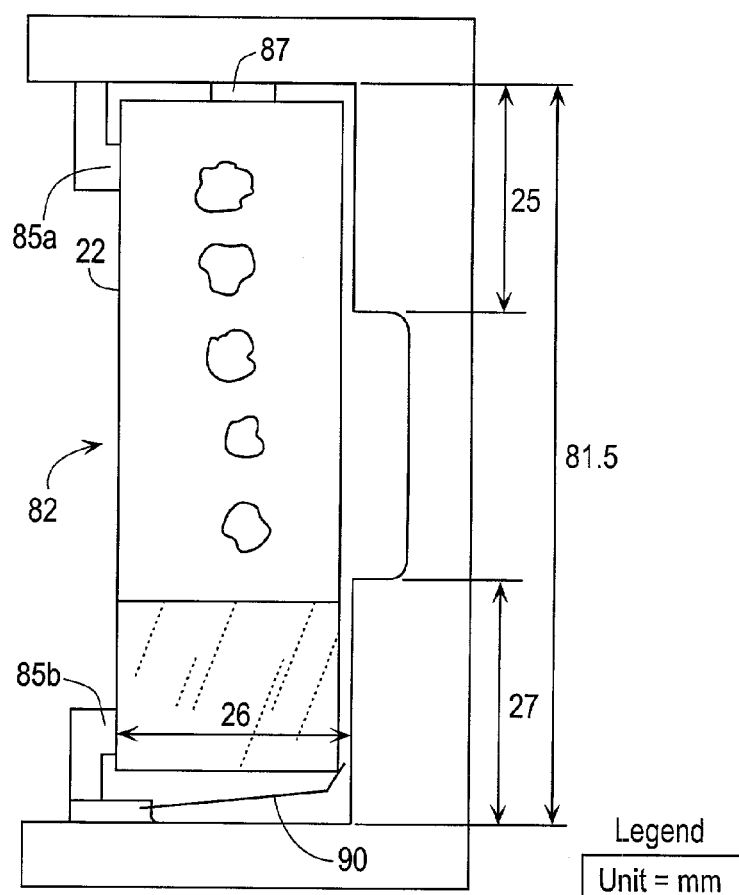
FIG. 3B is a detail view of one of the slide-receiving regions of the slide rack of FIG. 3A.

FIG. 3B is a detail view of one of the slide-receiving regions 82 of slide rack 80, showing the mechanism whereby the slide is reproducibly held in the holder. The slide is shown with five blobs schematically representing lymph node sections. The region surrounding the slide is formed with a pair of spaced lands 85*a* and 85*b* that engage one of the long edges of the slide, a land 87 that engages one of the short edges of the slide, and a spring 90 that urges the slide against lands 85*a*, 85*b*, and 87. In the particular orientation of FIG. 3B, the slide's long dimension extends vertically, lands 85*a* and 85*b* engage the left edge of the slide, land 87 engages the upper edge of the slide, and spring 90 is anchored near the lower left corner of the slide and urges the slide upwardly and to the left. The upper right corner of the slide is the most constrained, and defines a suitable origin for a slide-relative coordinate system.

A current implementation uses standard slides, but there is no reason that specially designed slides couldn't be used. For example, slides could be provided with unique barcodes for identification, and could have fiducial marks to facilitate location of the slide positions. If a barcode is placed on the end of each slide and digitized to determine the barcode location and orientation, it could form the basis for barcode-relative coordinates as an alternative to slide-relative coordinates. However, the present invention does not rely on such enhancements.

As shown, the slides have frosted areas at one end to allow handwritten markings to be placed on the slides, or to allow adhesive labels to be affixed. In the particular orientation of the drawing, the frosted areas are at the bottoms of the slides. In some implementations, it is preferred to mount the top row of slides with the frosted areas at the top, so that the samples on the slides are located closer to the center of the slide rack. This could be done to account for the fact that the scanner's area of maximum resolution is toward the center of the scanner bed. If desired, the slide rack could be fabricated so that the lands and springs were also reversed.

Computer System and Possible Architectures

Figure 4A:
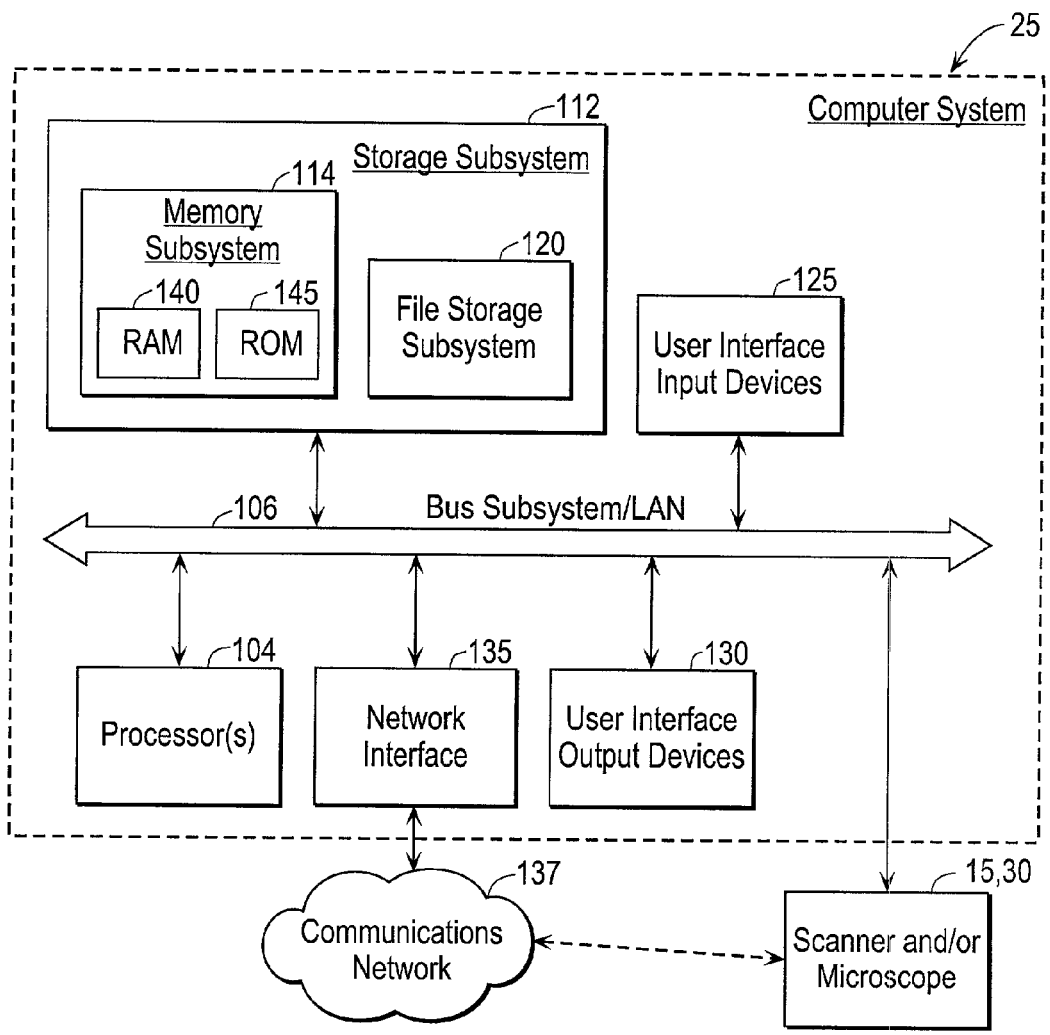
FIG. 4A is a block diagram of a representative computer system for use in embodiments of the present invention.

FIG. 4A is a simplified block diagram of a representative implementation of computer system 25 that can be used in conjunction with scanner 15 for carrying out various operations in support of the invention. Since the figure is drawn at a high level, it is labeled "Prior Art." When operating in the context of embodiments of the invention, such a computer system is not prior art. Computer system 25 typically includes at least one processor 104, which communicates with a number of peripheral devices via a bus subsystem 106. These peripheral devices typically include a storage subsystem 112, comprising a memory subsystem 114 and a file storage subsystem 120, user interface input devices 125, user interface output devices 130, and a network interface subsystem 135.

Bus subsystem 106 provides a mechanism for letting the various components and subsystems of computer system 25 communicate with each other as intended. The various subsystems and components of computer system 25 need not be at the same physical location but may be distributed at various locations on a local area network (LAN). Although bus subsystem 106 is shown schematically as a single bus, embodiments of the bus subsystem may utilize multiple buses.

The input and output devices allow user interaction with computer system 25. It should be apparent that the user may be a human user, a device, a process, another computer, and the like. Network interface subsystem 135 provides an interface to one or more networks, including an interface to a communications network 137, and is connected via such networks to corresponding interface devices in other computer systems. The network interface may include, for example, a modem, an Integrated Digital Services Network (ISDN) device, an Asynchronous Transfer Mode (ATM) device, a Direct Subscriber Line (DSL) device, a fiber optic device, an Ethernet card, a cable TV device, or a wireless device. The networks may be local area networks, wide area networks, or a collection of networks such as the internet.

User interface input devices 125 may include a keyboard, pointing devices such as a mouse, trackball, touchpad, or graphics tablet, a scanner, a barcode scanner for scanning slide barcodes (if used), a touchscreen incorporated into the display, audio input devices such as voice recognition systems, microphones, and other types of input devices. In general, use of the term "input device" is intended to include all possible types of devices and ways to input information into computer system 25 or onto communications network 137.

User interface output devices 130 may include a display subsystem, a printer, a fax machine, or non-visual displays such as audio output devices. The display subsystem may be a cathode ray tube (CRT), a flat-panel device such as a liquid crystal display (LCD), or a projection device. The display subsystem may also provide non-visual display such as via audio output devices. In general, use of the term "output device" is intended to include all possible types of devices and ways to output information from computer system 25 to a user or to another machine or computer system.

Storage subsystem 112 stores the basic programming and data constructs that provide the functionality of the computer system. For example, the various program modules and databases implementing the functionality of the present invention may be stored in storage subsystem 112. These software modules are generally executed by processor(s)

104. In a distributed environment, the software modules may be stored on a plurality of computer systems and executed by processors of the plurality of computer systems.

Memory subsystem 114 typically includes a number of memories including a main random access memory (RAM) 140 for storage of instructions and data during program execution and a read only memory (ROM) 145 in which fixed instructions are stored. File storage subsystem 120 provides persistent (non-volatile) storage for program and data files, and may include a hard disk drive, a floppy disk drive along with associated removable media, a compact disk read only memory (CD-ROM) drive, a rewritable optical drive, removable media cartridges, and other like storage media. One or more of the drives may be located at remote locations on other connected computers on the LAN or at another site on communications network 137, and may be shared by multiple computers.

Computer system 25 itself can be of varying types including a personal computer, a portable computer, a workstation, a computer terminal, a network computer, a mainframe, or any other data processing system. Due to the ever-changing nature of computers and networks, the description of computer system 25 depicted in FIG. 4A is intended only as a specific example for purposes of illustrating a representative configuration. In a specific implementation, scanner 15 was interfaced to a 933-MHz Power Mac G4 computer via a SCSI-2 interface. The computer was equipped with 512 Mbytes of memory and a 60-GByte disk drive for image storage.

Scanner 15 and/or microscope 30 are shown connected to bus subsystem 106, which as mentioned above can also include a local area network. The scanner and/or microscope could also be connected to computer system 25 from remote locations; a connection to the computer system via communications network 137 is shown in phantom. It should be understood that the computer that controls the scanner need not be the same computer that processes the scanned images. Similarly, the computer that processes the images need not be the same computer that maintains database 27. Moreover, the scanner and the microscope may be at remote locations from each other, so it may be yet another computer that controls the microscope.

Figure 4B:
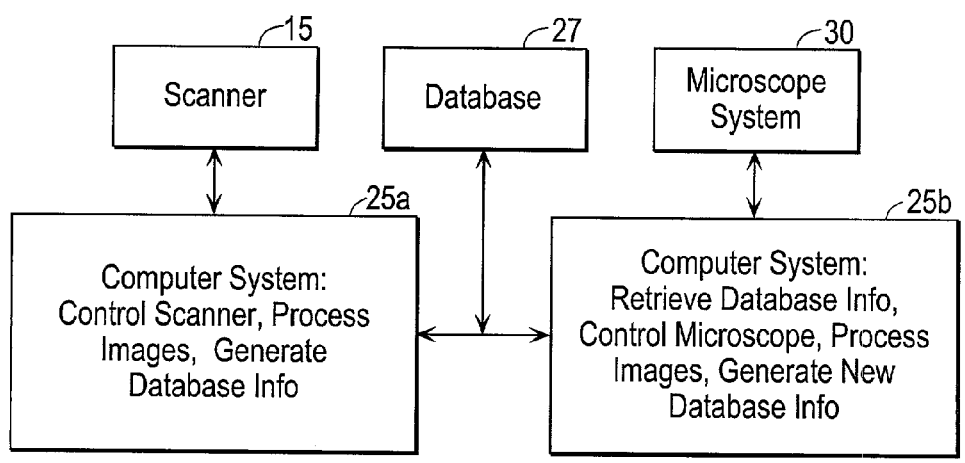
FIG. 4B is a block diagram of a representative distributed computer system for use in embodiments of the present invention.

FIG. 4B is a block diagram of a distributed computer system that reflects a typical division of labor between the person (typically a laboratory technician) who operates the scanner and makes sure that images of suitable quality are obtained, and the person (typically a pathologist) who examines the candidates to eliminate false positives. Scanner 15 is connected to a first computer system 25a, with which the technician interacts to control the scanner and acquire the images. This computer system also performs the image analysis and generates the information for database 27.

Computer system 25a is connected to a second computer system 25b, which can be connected to microscope system 30. Computer system 25b is typically located at a different physical location from computer system 25a, and is used by the pathologist to access candidates from the database for examination. This examination is first performed by viewing the high-resolution scanned images on the monitor of computer system 25b, and subsequently for at least some candidates, by re-examining the slides at higher resolution on microscope system 30. As will be discussed further below, computer system 25b may also perform additional image analysis (say of high-resolution microscope images) and store additional information in database 27. Database 27 is shown connected to both computers, but is not necessarily a part of either. The particular structure and location of database 27 are not part of the invention, and will not be described in detail. It is noted, however, that a SQL database is preferred, but it is also contemplated that at the stage of initially acquiring data for the database, the data may be stored in any convenient intermediate format, for example, a spreadsheet, and later imported into the database.

Microscope System

Figure 5:
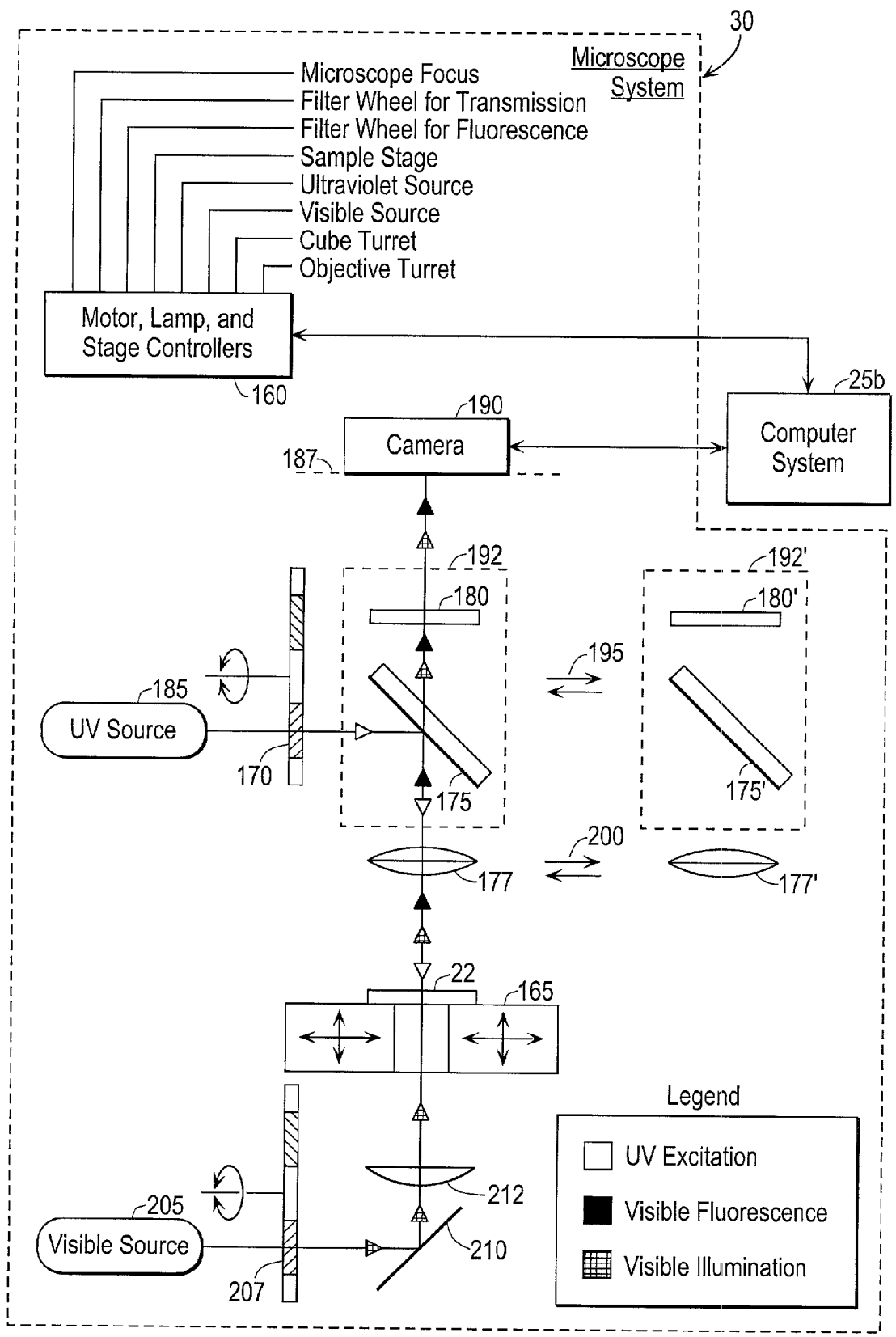
FIG. 5 is an optical schematic of a scanning microscope suitable for use as an adjunct to the present invention.

FIG. 5 is an optical schematic of a conventional microscope scanner (CMS) implementation of microscope 30 suitable for use as an adjunct to the present invention, namely in subsequent analysis of samples on slides based on initial analysis of the images obtained using scanner 15. Suitable CMS systems are marketed by Applied Imaging Corporation under the trademark MDS. As mentioned above, the present invention can also be used in conjunction with a standard (non-scanning) microscope.

The microscope is shown as being set up for carrying out brightfield (transmission) and/or fluorescence imaging of a slide 22. It is noted that there may be no need to provide fluorescent image capability, in which case portions of the optical train would not come into play, or may be absent entirely. Also, a number of the elements are shown as being under computer control through a controller block 160 interfaced to computer system 25b. This is merely a preferred capability in a CMS, and is not necessary for the invention.

The slide is shown mounted to a stage 165, which provides three-dimensional rectilinear motion. Some stages can also provide rotational motion. While a single slide 22 is shown on the stage, the stage may be configured to handle an array of slides. Such a stage would typically include a first-level stage having a relatively large range of motion and a relatively coarse resolution, and a second-level stage having a relatively small range of motion and a relatively fine resolution.

The portion of the optical train for epi-illuminated fluorescence imaging includes an excitation filter 170 (shown as one of several such filters on a filter wheel), a polychroic mirror 175, a microscope objective 177 (say 10–100x), and an emission filter 180. The fluorescent optical train is set up with a multiband emission filter and a polychroic mirror so that multiple fluorescent images can be acquired without changing the mirror or emission filter.

Excitation radiation (shown schematically by hollow arrowheads) from an ultraviolet (UV) source 185 passes through excitation filter 170, is largely reflected by mirror 175 and proceeds through microscope objective 177 to slide 22. Fluorescent radiation (shown schematically by solid black arrowheads) emitted from the sample on slide 22 passes back through objective 177, through mirror 175, and through emission filter 180 to form an image in an image plane 187. The image is digitized by a CCD video camera 190 and the digitized image is sent to computer system 25b for subsequent processing. As mentioned above, computer system 25b is also used to control various components in the system.

Polychroic mirror 175 and emission filter 180 are typically rigidly mounted to a supporting structure 192 (shown in phantom); the assembly is often referred to as a cube, with additional cubes (e.g., 192') being movable into and out of the optical path. Oppositely directed arrows 195 represent a suitable mechanism such as a rotatable turret or a detented slide mechanism. The multiple excitation filters are typically deployed on a rotatable filter wheel (as shown). In a typical microscope, objective lens 177 will be one of several (e.g., objective lens 177') mounted on a turret or like structure. This is shown schematically by oppositely directed arrows 200.

The portion of the optical train for the brightfield imaging includes a visible light source 205, a passband filter 207 (shown as one of several such filters on a filter wheel), a mirror 210, and a condenser 212. Illumination radiation from source 205 passes through passband filter 207, is reflected by mirror 210 to condenser 212. The radiation passing through the condenser illuminates slide 22, and proceeds through microscope objective 177. The illumination radiation (shown schematically by hatched arrowheads) is in a wavelength range that passes through polychroic mirror 175 and emission filter 180.

Representative Sample Preparation

The present invention, in its broader aspects, is not limited to any particular type of sample or any particular type of sample preparation. However, the examination of lymph nodes for micrometastatic cells is a good example of an application where the present invention allows the meaningful examination of a large number of sections (samples) in a reasonable time, a feat that has remained largely impractical using conventional techniques.

The samples were obtained from material taken in a study by Liefers et al. (LIEFERS-1998), which analyzed 246 lymph nodes from 26 patients with TMN stage II colorectal cancer. The lymph nodes were obtained consecutively from curative resections performed at the Department of Surgery of the Leiden University Medical Center between January 1990 and February 1992. Preoperative and perioperative examinations showed no evidence of metastatic disease. Follow-up was carried out in accordance with the department's protocol and was based on periodic evaluations of the patient. The follow-up findings were confirmed in all patients as of Feb. 1, 2002. After 10 years, paraffin blocks from lymph nodes were still available from 20 patients (out of the original 26).

In the original Liefers study, half of the node was fixed in formalin and embedded in paraffin for routine histopathological examination. The other half of the resected node was used for RNA isolation for the analysis of Carcinoembryonic Antigen (CEA)-Specific mRNA using reverse transcriptase polymer chain reaction (RT-PCR). For the present study all available lymph nodes were analyzed for the 8 patients who were originally PCR-positive for CEA. From the PCR-negative group of 12 patients, six lymph nodes were chosen randomly to match the average number of nodes in the positive group. From this material serial sections were cut at intervals of 200 μm. Each serial section included ten adjacent 5-μm sections. This resulted in approximately 80 sections per lymph node.

The sections were hydrated and subjected to natriumcitrate (pH 6.0 at 100° C.) for 10 minutes prior to exposure to the primary monoclonal cytokeratin antibody AE1/AE3. Anti-AE1/AE3is a pan-specific cocktail of antibodies for human cytokeratins available from DAKO Corporation, 6392 Via Real, Carpinteria, Calif. 93013. Immunostaining was based on the avidin-biotin-peroxidase technique using 3,3"-diaminobenzidine (DAB) endpoint. This treatment selectively stains cytoplasm expressing cytokeratin with a brown color. All sections were briefly counterstained with hematoxylin, which stains cell nuclei with a blue color.

Image Processing

As will be described below, a number of the automated image processing steps include comparing pixel values against thresholds to determine whether a given pixel is part of a candidate. As part of calibrating the software (i.e., determining appropriate parameter values), lymph node material from a patient with known occult tumor cells was used to set the thresholds for the selection criteria. The samples were prepared as described above.

Figure 6:
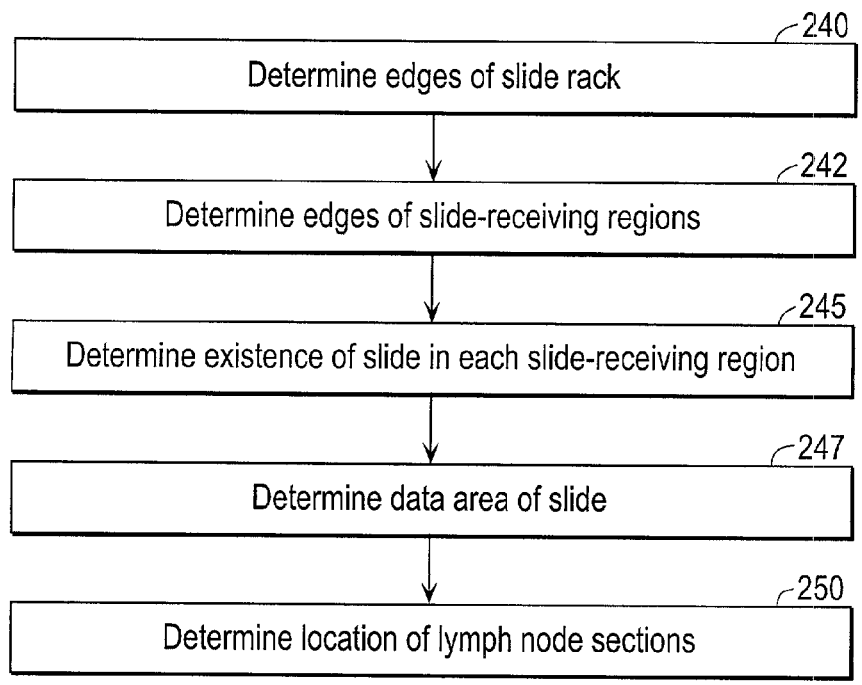
FIG. 6 is a flowchart showing a specific way to determine the locations of the slides on the scanner bed and the locations of the image crops in the low-resolution images.

FIG. 6 is a flowchart showing the details in step 40 of determining the locations of the slides on the scanner bed and the locations of the image crops in the low-resolution scan image. First, the outer edges of slide rack 80 are determined (step 240) using a global threshold. Thereafter, the inner edges of slide-receiving regions 82 are detected (step 242) to provide reference information allowing subsequent relocation of the slides. The coordinates of the corners of the slide-receiving regions are also used to compute and thus account for the angle between the slide rack and the x-y coordinates of the scanner.

It is then determined (step 245) whether there is a slide within each slide-receiving region. This can be accomplished many different ways, the simplest being by comparing the average density over the nominal slide region (i.e., an area having boundaries inwardly displaced from the inner edges of the slide-receiving region) to a threshold. The details can vary depending on the nature of the slide samples and any characteristic features possessed by blank slides. For example, some samples are known to have extended areas that are not completely transparent (as is the case for lymph node sections), and some blank slides are known to have frosted areas for handwritten notations. In general, it is relatively straightforward to detect any departure from substantially uniform transparency.

For those slide-receiving regions that contain slides, the data area of the slide is determined (step 247). This is straightforward, and depends on the particulars of the slides. As mentioned above, some slides have known frosted areas, and plain slides may have self-adhesive labels that are applied to a designated area at the time of the sample preparation.

The locations of the image crops are then determined (step 250). Lymph nodes are initially detected by a global threshold, which is calculated by searching for the optimal value between the object and background peak of the gray-value histogram of pixel intensities. Small holes remaining after thresholding are filled by morphological image transformations (morphological close or dilation operations) to remove small objects, mostly corresponding to fat tissue. A lymph node is characterized by a typical size and shape, and so connected components that are too small in one or both dimensions are rejected, and the smallest enclosing rectangle for each remaining connected component is determined and its coordinates stored.

As a matter of design choice, steps 242, 245, 247, and 250 can be performed sequentially for each individual slide-receiving region, or each step can be performed for all the slide-receiving regions in the rack before proceeding to the next step. Further, while the above-described sequence is preferred for efficiency reasons, there is no fundamental reason why step 245 of determining whether there is a slide in a given slide-receiving region can't be determined after processing the entire region for connected components. Background information on morphological image processing and determining bounding boxes for connected components can be found in U.S. Pat. No. 5,065,437 to Dan S. Bloomberg.

Figure 7:
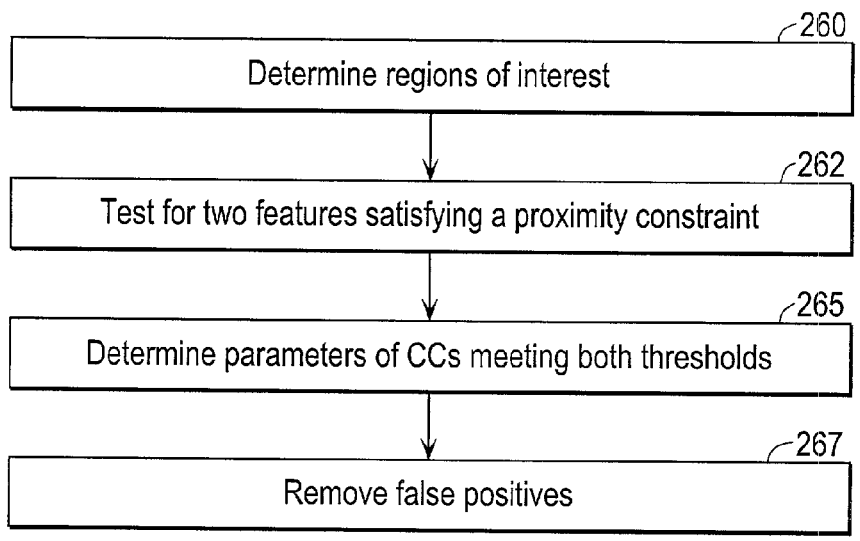
FIG. 7 is a flowchart showing a specific way to find candidate structures of interest in the high-resolution image crops.

FIG. 7 is a flowchart showing the details in step 50 of finding candidate structures of interest in the high-resolution image crops. As mentioned above, the high-resolution scan preferably also digitizes regions at the edges of the slides in addition to digitizing the image crops. This is to accurately identify the location and angular orientation of the individual slides, which information is used to convert scanner coordinates of image objects to slide-relative coordinates. If one row of the slides were oriented oppositely to the other two rows as discussed above, this would be taken into account in converting the scanner coordinates to slide-relative coordinates (since the orientation of the slides on the scanner would not normally be remembered once the slides have been removed from the slide rack).

A typical image crop for a lymph node section is on the order of 6×6 mm, which translates to on the order of 1300×1300 pixels when sampled at 5600 dpi. Therefore, it may be convenient to subdivide the image crops into smaller image areas (say by a factor of three in each dimension) for better performance. These smaller image areas would overlap slightly so that a candidate would be always be entirely in one of the image areas.

Again, for better performance, a relatively simple (and thus fast) test is performed in a given image crop, or reduced area thereof, to determine regions of interest (step 260). This reduces (perhaps by a factor of 2–4) the portion of the image crop that needs to be subjected to the more intensive image processing operations that follow. In one implementation, selecting the regions of interest entails selecting only those areas where a predetermined number (e.g., two or four) of adjacent pixels are above a threshold and are of a generally red color (i.e., R>B and R>G where R, G, and B are the scanner values for a given pixel). Portions of the image crop outside the regions of interest are generally not subjected to further processing.

Each region of interest is subjected to testing whether two features satisfy a proximity constraint (step 265). A cell is considered a candidate if its cytoplasm expresses cytokeratin, which is manifested by its pixels lying within a given first region of color space. Similarly, hematoxylin-counterstained cell nuclei will have pixels lying within a given second region of color space (distinct from the given first region). On the other hand, pixels not associated with cytokeratin expression might nevertheless lie within that given first region, and pixels not associated with a cell might nevertheless lie within that given second region. Therefore, a candidate must satisfy the constraint that it has a pixel lying within the given first region of color space that is within a predetermined spatial distance of a pixel lying within the given second region of color space. Put another way, a pixel having a color potentially representing cytokeratin expression must be within a predetermined distance of a pixel having a color potentially representing a counterstained nucleus.

The color space and the thresholding can be carried out in any convenient color space. Scanners typically provide red, green, and blue (RGB) tristimulus values, but these scanner values can be transformed to other color coordinates such as XYZ, CIE xyY, and CIE Yuv. In any event, as mentioned above, the regions of color space are preferably determined with reference to known positive candidates (a learning set) based on a similar sample preparation.

Once the candidates are identified, their parameters are determined (step 265). This entails measuring such parameters as area, average density, the peak density, shape (e.g., eccentricity), and color. As mentioned, the color can be expressed in any convenient color coordinate system. Given the spatial resolution (a single cell sometimes contained fewer than 10 pixels), and since it is desired to detect larger groups of micrometastatic cells, the averaged color appeared to be the best selection parameter in this study. Based on the automatically measured parameters of the candidates, false positives are removed (step 267). It is also desirable to store an overview image of the lymph node section with the gallery images in the database, and to provide markers of the locations where the candidates were found.

There is an indication that a comparison between successive slices can be used to reduce the number of false positives. Simply put, if a candidate is found at essentially the same location in successive slices, it is much less likely to be an artifact. While this is easy to determine by human visual inspection, automating this aspect requires additional steps to register the slices. For example, contour analysis can provide a figure of merit as to the degree of contour match, and would provide more reliable matching than simply registering the centers of gravity of two successive slices. A preferred technique from the point of view of matching accuracy is to provide extra markers in the paraffin block in which the node was originally embedded, but this does require more work during the sample preparation.

Slide Relocation

The images of candidate cells of interest captured by scanner 15 are at relatively low magnification (equivalent to about 2.5×) and may contain insufficient detail for a pathologist/clinician to decide if the candidate is a real tumor cell or an artifact. Although slide relocation is not necessarily part of the invention, one aspect of the invention is to provide sufficient information that a sample can be placed on a microscope and rapidly positioned to allow examination of candidates at a higher resolution (say at a magnification of 10–100×, which is 4–40 times the resolution than that provided by scanner 15). If higher magnification images of the candidates are required, the slides analyzed on the flatbed scanner can be transferred to microscope 30.

If microscope 30 is a standard (non-scanning) microscope, coordinates of the candidates are provided in a pre-established frame of reference (e.g., using an "England Finder") and the positions of the candidates relocated manually by the operator. An England Finder is a third-party slide with etchings that establish a coordinate system.

If microscope 30 is a CMS such as illustrated in FIG. 5, the slide is mounted on motorized stage 165 and is repositioned to the location of the selected candidate to allow recapture at high magnification. The relocation is achieved by converting the slide-relative candidate coordinates determined in step 50 of FIG. 2 (step 265 of FIG. 7) to motorized stage coordinates. The transformation matrix to achieve this is determined by prior analysis of a calibration slide on the CMS.

If the relocation accuracy is too low for a high-magnification objective, an additional strategy may be employed. The slide can be relocated on the CMS and an image of the slide captured at low magnification. The chosen cell can be identified again in this image, using the same image analysis techniques employed earlier, and its new coordinates used to adjust the stage position for accurate relocation at high magnification. It would typically only be necessary to scan a few of the microscope fields to find the candidate. The final high-resolution image of the suspected tumor cell can be captured and stored in database 27. This image or, if preferred, the view down the microscope should allow the pathologist to accurately classify the suspect cell.

Microscope 30 provides a secondary system that allows subsequent examination of one or more of the slides where it is believed that the information from the stored image information of the candidate is not sufficient. While the microscope may be selected because it provides higher resolution than the high-resolution scan of scanner 15, it may be that microscope 30 is selected because it provides some additional capability other than higher resolution. For example, the scanner provides a particular illumination regime suitable for recognizing candidate structures of interest in samples stained in a particular way. As mentioned above, the microscope may also provide additional viewing capability, say for fluorescent dyes or for additional brightfield illumination schemes, which may be useful at the same resolution as the scanner resolution.

Experimental Results

The following table shows the representative times taken to perform the operations based on 80 sections (image crops) per lymph node (5 sections per slide) with each section being on the order of 6×6 mm and being sampled at 5600 dpi.

| Low-Resolution Scan | |
| --- | --- |
| Acquire low-resolution image of slide rack | 50 seconds |
| Determine image crop locations | 10 seconds |
| Total for low-resolution scan | 60 seconds |
| High-Resolution Scan (per image crop) | |
| Calibrate scanner and focus image crop | 45 seconds |
| Scan image crop to disk | 13 seconds |
| Analyze image crop | 2 seconds |
| Total for one image crop | 60 seconds |
| Total for one lymph node (low-resolution scan and 80 image crops) | 81 minutes |

In short, using the materials from the Liefers study, it was found that the use of the flatbed scanner provides increased sensitivity in the detection of micrometastases with a throughput that makes examination of an entire lymph node practical.

All the slides were first manually examined by conventional microscopy (as noted in the introduction, this would normally not be practical). A node was called positive when at least one IHC positive cell was found (excluding white blood cells, macrophages, and the like, which are known for non-specific staining) and confirmed by a second independent person (pathologist). Subsequently, the sections were recorded using the flatbed scanner and subjected to the automated analysis as detailed above. The location of all manually detected positive cells was marked on print-outs of the recorded images and compared to the automated analysis.

For the complete study, 4569 paraffin sections were automatically analyzed, which included a total of 33 positive nodes that were analyzed. Two nodes (each containing only one positive cell) were missed using the automated analysis. However, these nodes belonged to patients who had 3 more nodes in which occult tumor cells were detected by the automated analysis. Further, one patient was missed in the manual examination but found positive upon visual verification of the candidate cells after the automated analysis.

REFERENCES

LIEFERS-1998: "Micrometastases and survival in stage II colorectal cancer," G-J. Liefers, A-M Cleton-Jansen, C. J. H. van de Velde, J. Hermans, J. H. J. M van Krieken, C. J. Cornelisse, R. A. E. M. Tollenaar, *N. Eng. J Med., July* 1998.

CONCLUSION

Flatbed scanners have not been designed for the purpose of producing digital images of biological samples for subsequent analysis and classification. However, the present invention is able to use such scanners to enable the automated analysis of a large number of samples with a practical throughput. This has potentially immense consequences in many high-volume scanning applications. In particular, the invention makes it possible to quickly analyze the large number of slides per patient created by the serial sectioning described above. While the results reported above used materials from a well documented selection of colorectal patients, a similar approach would apply for breast cancer or melanomas where lymph node involvement and particularly the role of the sentinel node is an important element. While lymph node sections were described, other pathology samples could be rapidly analyzed.

While the above is a complete description of specific embodiments of the invention, various modifications, alternative constructions, and equivalents may be used. For example, while representative computer and microscope systems were described, suitable systems could include additional or fewer elements than the systems described. Similarly, while specific image processing techniques were described, there are various alternative techniques. Additionally, while the particular samples were tissue sections, the invention could be used to analyze tissue microarrays. Indeed, the samples need not be of human origin, but could be animal or plant cells or tissues.

Additionally, while the first and second scans were described as occurring at first and second resolutions where the second resolution is higher than the first, it is also possible that the scans could be at the same resolution with different sets of scanner parameters. The first set of scanner parameters in the first scan could be optimized for rapid processing of the image data to find the samples, and the second set of scanner parameters in the second scan could be optimized for optimum detection of the candidates.

Moreover, while current scanner technology provides a lower resolution than current microscope technology, it is possible that the secondary system on which slides are relocated is another scanner, say a slide scanner having a higher resolution, but incapable of providing the throughput of the flatbed scanner. Indeed, there are scenarios where the same scanner could be used for subsequent imaging, perhaps using different scanning parameters or a higher resolution (if available).

Therefore, the above description should not be taken as limiting the scope of the invention as defined by the claims.

What is claimed is:

1. A method of analyzing histology or cytology samples positioned on slides, the method comprising:
scanning a plurality of slides with a flatbed scanner using a first set of scanner parameters to capture first image data;
analyzing the first image data to determine the locations on the slides that potentially contain the samples;
scanning at least those portions of the slides that potentially contain the samples with the flatbed scanner using a second set of scanner parameters to capture second image data that contains additional information regarding the samples;

analyzing the second image data to produce information including coordinate information about candidate structures of interest in the sample, the information being referred to as candidate information; and storing the candidate information for later presentation.

2. The method of claim 1 wherein:
the first set of scanner parameters allows rapid determination of the location of the samples; and
the second set of scanner parameters allows the determination of the candidate information.

3. The method of claim 1 wherein:
the first set of scanner parameters is characterized by a first resolution; and
the second set of scanner parameters is characterized by a second resolution that is higher than the first resolution.

4. The method of claim 1, and further comprising:
for each of at least some candidate structures of interest, storing at least a portion of the second image data that includes that candidate structure of interest; and
displaying at least one stored portion of the second image data that contains a candidate structure of interest.

5. The method of claim 1, and further comprising:
positioning one of the slides that has been determined to contain a candidate structure of interest on a stage; and
using the coordinate information for that candidate structure of interest to position the slide so that the portion of the slide that corresponds to the portion of the second image data containing the given candidate structure of interest is aligned with a field of view of a microscope.

6. The method of claim 5 wherein the coordinate information is electronically transferred to a computer that controls the stage.

7. The method of claim 5 wherein the coordinate information is used in conjunction with a reference/finder grid.

8. The method of claim 1, and further comprising:
retrieving the candidate information generated by analyzing the second image data; and
transferring the coordinate information for candidate structures of interest to a secondary higher magnification system for further analysis of slides containing the candidate structures of interest.

9. The method of claim 1 wherein the samples are one of the group consisting of tissue sections, tissue microarrays, cells containing metaphase chromosomes or metaphase spreads, and prokaryotic cells.

10. The method of claim 1 wherein the structures of interest in the samples are cancer cells.

11. The method of claim 1 wherein the samples are not of human origin but are animal or plant cells or tissues.

12. A method of analyzing histology or cytology samples positioned on slides, the method comprising:
scanning a plurality of slides at a first resolution with a flatbed scanner to capture first image data;
analyzing the first image data to determine the locations on the slides that potentially contain the samples;
scanning at least those portions of the slides that potentially contain the samples at a second resolution that is higher than the first resolution on the flatbed scanner to capture second image data;
analyzing the second image data to produce information, referred to as candidate information, that includes, for each candidate structure of interest, coordinate information for that candidate structure of interest and additional attribute information for that candidate structure of interest; and
storing the candidate information for later presentation.

13. The method of claim 12, and further comprising:
retrieving the candidate information generated by analyzing the second image data; and
transferring the coordinate information for candidate structures of interest to a secondary higher magnification system for further analysis of slides containing the candidate structures of interest.

14. The method of claim 13 wherein:
the secondary system includes a computer-controlled microscope; and
the coordinate information is used by a computer in the secondary system to control a stage for positioning the slides containing the candidate structures of interest.

15. The method of claim 13 wherein:
the secondary system includes a non-scanning microscope; and
the coordinate information is transferred for manual relocation using a reference/finder grid.

16. The method of claim 12 wherein the samples are one of the group consisting of tissue sections, tissue microarrays, cells containing metaphase chromosomes or metaphase spreads, and prokaryotic cells.

17. The method of claim 12 wherein the structures of interest in the sample are cancer cells.

18. The method of claim 12 wherein the samples are not of human origin but are animal or plant cells or tissues.

19. A method of analyzing histology or cytology samples positioned on slides to determine candidate structures of interest, the method comprising:
imparting optical properties to objects in the samples so that structures of interest can be recognized by a unique combination of features under specific illumination;
scanning a plurality of slides at a first resolution with a flatbed scanner that provides the specific illumination to capture first image data;
analyzing the first image data to determine the locations on the slides that potentially contain the samples;
scanning at least those portions of the slides that potentially contain the samples at a second resolution that is higher than the first resolution on the flatbed scanner to capture second image data;
analyzing the second image data to find instances of the unique combination of features satisfying a proximity constraint, such instances being designated candidate structures of interest;
for each of at least some candidate structures of interest, further analyzing the candidate structure of interest to determine at least one characteristic thereof, and
storing candidate information that includes (a) coordinate information of the candidate structure of interest, (b) the at least one characteristic of the candidate structure of interest, and (c) a portion of the second image data containing the candidate structure of interest; and
for each of at least some slides,
retrieving candidate information for a candidate structure of interest on the slide, and
using the coordinate information of the candidate structure of interest to position the slide relative to a secondary system for further analysis.

20. The method of claim 19 wherein:
the secondary system includes a computer-controlled microscope; and
the coordinate information is used by a computer in the secondary system to control a stage for positioning the slides containing the candidate structures of interest.

21. The method of claim 19 wherein:
the secondary system includes a non-scanning microscope; and
the coordinate information is transferred for manual relocation using a reference/finder grid.

22. The method of claim 19 wherein the samples are one of the group consisting of tissue sections, tissue microarrays, cells containing metaphase chromosomes or metaphase spreads, and prokaryotic cells.

23. The method of claim 19 wherein the structures of interest in the sample are cancer cells.

24. The method of claim 19 wherein the samples are not of human origin but are animal or plant cells or tissues.

25. A method of analyzing histology or cytology samples positioned on slides stained to produce enough brightfield contrast to allow recognition of one or more structures of interest in the samples, the method comprising:
scanning the slides with a flatbed scanner to capture digital image data;
storing the position coordinates and images of the cells of interest for further review;
finding the cells of interest by coordinates and further analyzing the cells and capturing additional images at the same or higher magnification or resolution;
analyzing the captured images to produce relevant information on the morphology and reactivity of the analyzed markers on the sample; and
transferring coordinates of areas of interest, derived from analyzing captured images, to a secondary higher magnification system for further analysis and operator review; and
presenting this information to the operator.

26. A method of analyzing histology or cytology samples positioned on one or more slides, the method comprising:
staining the slide with one or more relevant markers to produce enough brightfield contrast to allow recognition of one or more structures of interest in the one or more samples;
scanning the one or more slides and capturing images with a flatbed scanner;
storing the captured images for each of the slides;
analyzing the captured images to produce relevant information on the morphology and/or color of the structures of interest on the sample; and
presenting this information to the operator.

27. A method of analyzing histology and cytology samples positioned on one or more slides, the method comprising:
staining the one or more slides with one or more relevant markers to produce a enough brightfield contrast to recognize one or more structures of interest in the one or more samples;
scanning the one or more slides and capturing images with a flatbed scanner;
storing the position coordinates and images of the cells of interest for further review;
finding the cells of interest by coordinates and further analyzing the cells and capturing additional images at the same or higher magnification or resolution;
analyzing the captured images to produce relevant information on the morphology and reactivity of the analyzed markers on the sample; and
transferring coordinates of areas of interest, derived from analyzing captured images, to a secondary higher magnification system for further analysis and operator review; and
presenting this information to the operator.

28. A method of analyzing histology or cytology samples positioned on one or more slides, the samples having been stained with one or more relevant markers to produce enough brightfield contrast to recognize one or more structures of interest in the one or more samples, the method comprising:
using a flatbed scanner to generate one or more images of at least portions of the one or more slides;
storing the images;
analyzing the images to identify sufficiently large connected components as possible structures of interest;
analyzing connected components so identified using at least one of morphology and color of such connected components to identify possible structures of interest; and
storing information on the location and the morphology and/or color of the possible structures of interest on the sample.

29. The method of claim 28, and further presenting this information to the operator.

30. A method of analyzing a histology or cytology sample positioned on a slide, the sample having been stained with one or more relevant markers to produce enough brightfield contrast to recognize one or more structures of interest in the one or more samples, the method comprising:
using a flatbed scanner to acquire a first image of the slide at a first resolution;
using a computer to analyze the first image to determine a region of interest of the slide;
using the scanner to acquire a second image of the region of interest at a second resolution that is higher than the first resolution;
using the computer to analyze the second image to determine one or more features in the second image that are candidates for being structures of interest;
using the computer to generate position information for each feature;
using the computer to generate additional information that characterizes an attribute of each feature; and
storing the position information and attribute information for each feature.

31. A method of analyzing histology or cytology samples positioned on slides, the method comprising:
scanning a plurality of slides with a flatbed scanner at a first resolution to capture first image data;
analyzing the first image data to determine the locations of the slides and the locations on the slides that potentially contain the samples;
scanning at least those portions of the slides that potentially contain the samples with the flatbed scanner at a second resolution that is higher than the first resolution to capture second image data that contains additional information regarding the samples;
analyzing the second image data to produce information including coordinate information about candidate structures of interest in the sample, the information being referred to as candidate information; and
storing the candidate information for later presentation.

32. The method of claim 31 wherein the slides are located in a slide rack having slide rack edges and a plurality of slide-receiving regions.

33. The method of claim 32 wherein analyzing the first image data comprises:
determining the edges of the slide rack;
determining the edges of the slide-receiving regions;
determining the existence of a slide in each slide-receiving region;

determining the data areas of slides that are present in the slide rack; and determining, within the data areas, the locations that potentially contain the samples.

34. The method of claim 31 wherein analyzing the second image data comprises, for at least those portions of the slides that potentially contain the samples:

determining regions of interest; and testing, within the regions of interest, for two features satisfying a proximity constraint, thereby signifying a candidate structure of interest.

35. The method of claim 34 wherein analyzing the second image data further comprises determining parameters of the candidate structures of interest.

36. The method of claim 31, and further comprising:

for each of at least some candidate structures of interest, storing at least a portion of the second image data that includes that candidate structure of interest; and displaying at least one stored portion of the second image data that contains a candidate structure of interest.

positioning one of the slides that has been determined to contain a candidate structure of interest on a stage; and using the coordinate information for that candidate structure of interest to position the slide so that the portion of the slide that corresponds to the portion of the second image data containing the given candidate structure of interest is aligned with a field of view of a microscope.

37. The method of claim 31 wherein the samples are one of the group consisting of tissue sections, tissue microarrays, cells containing metaphase chromosomes or metaphase spreads, and prokaryotic cells.

38. The method of claim 31 wherein the structures of interest in the samples are cancer cells.

* * * * *